(12) United States Patent
Kirschman

(10) Patent No.: US 9,486,263 B2
(45) Date of Patent: Nov. 8, 2016

(54) SCREW IMPLANT AND SYSTEM AND METHOD FOR LOCKING A SCREW IN AN IMPLANT PLATE

(71) Applicant: David Louis Kirschman, Dayton, OH (US)

(72) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 248 days.

(21) Appl. No.: 14/026,405

(22) Filed: Sep. 13, 2013

(65) Prior Publication Data

US 2014/0012329 A1 Jan. 9, 2014

Related U.S. Application Data

(63) Continuation-in-part of application No. 12/612,209, filed on Nov. 4, 2009, now Pat. No. 8,535,356.

(51) Int. Cl.
*A61B 17/86* (2006.01)
*A61B 17/80* (2006.01)
*A61B 17/88* (2006.01)

(52) U.S. Cl.
CPC ....... *A61B 17/8605* (2013.01); *A61B 17/8052* (2013.01); *A61B 17/8615* (2013.01); *A61B 17/888* (2013.01)

(58) Field of Classification Search
CPC ............ A61B 17/861–17/862; A61B 17/8052
See application file for complete search history.

(56) References Cited

U.S. PATENT DOCUMENTS

| | | |
|---|---|---|
| 4,488,543 A | 12/1984 | Tornier |
| 5,192,327 A | 3/1993 | Brantigan |
| 5,261,911 A | 11/1993 | Carl |
| 5,549,612 A | 8/1996 | Yapp et al. |
| 5,713,899 A | 2/1998 | Marnay et al. |
| 5,776,196 A | 7/1998 | Matsuzaki et al. |
| 6,136,002 A | 10/2000 | Shih et al. |
| 6,159,245 A | 12/2000 | Meriwether et al. |
| 6,224,602 B1 | 5/2001 | Hayes |
| 6,258,089 B1 | 7/2001 | Campbell et al. |
| 6,261,586 B1 | 7/2001 | McKay |
| 6,264,655 B1 | 7/2001 | Pisharodi |

(Continued)

FOREIGN PATENT DOCUMENTS

| | | |
|---|---|---|
| DE | 10101267 | 7/2002 |
| EP | 1561429 | 8/2005 |
| FR | 2856272 | 12/2004 |

*Primary Examiner* — David Bates
*Assistant Examiner* — Olivia C Chang
(74) *Attorney, Agent, or Firm* — Jacox, Meckstroth & Jenkins

(57) ABSTRACT

A plate system and method comprising a plate and a screw having an integral resilient lock. The screw comprises a head that has a portion that is adapted to be compressible as it is screwed into bone using a tool. After the screw head is received in the plate and the tool is removed therefrom, the screw head decompresses or expands into a locking or receiving area, thereby locking the screw in the plate. The plate is adapted to have at least one or a plurality of detents or lips for cooperating with at least a portion of the screw head to retain the screw in the plate and prevent it from withdrawing therefrom.

35 Claims, 8 Drawing Sheets

(56) References Cited

U.S. PATENT DOCUMENTS

| | | |
|---|---|---|
| 6,306,136 B1 | 10/2001 | Baccelli |
| 6,328,738 B1 | 12/2001 | Suddaby |
| 6,361,537 B1 | 3/2002 | Anderson |
| 6,592,586 B1 | 7/2003 | Michelson |
| 7,955,362 B2 | 6/2011 | Erickson et al. |
| 8,361,126 B2 | 1/2013 | Perrow et al. |
| 8,535,356 B2 | 9/2013 | Kirschman |
| 2008/0097444 A1 | 4/2008 | Erickson et al. |
| 2009/0062862 A1 | 3/2009 | Perrow et al. |
| 2010/0042162 A1* | 2/2010 | Edie .............. A61B 17/861 |
| | | 606/301 |
| 2011/0106171 A1 | 5/2011 | Kirschman |
| 2011/0160776 A1 | 6/2011 | Erickson et al. |
| 2013/0131685 A1 | 5/2013 | Perrow |

* cited by examiner

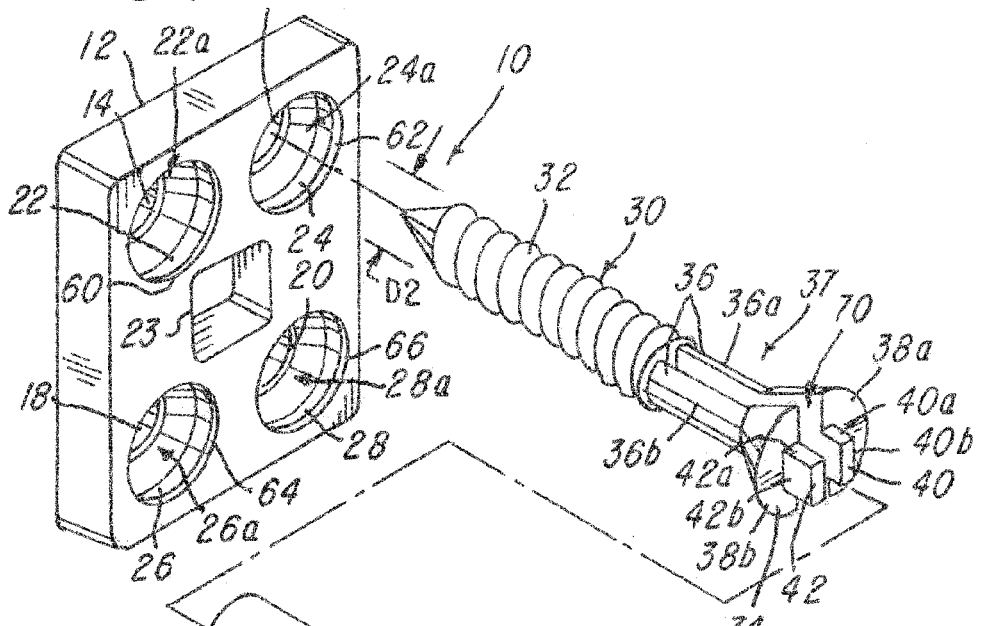
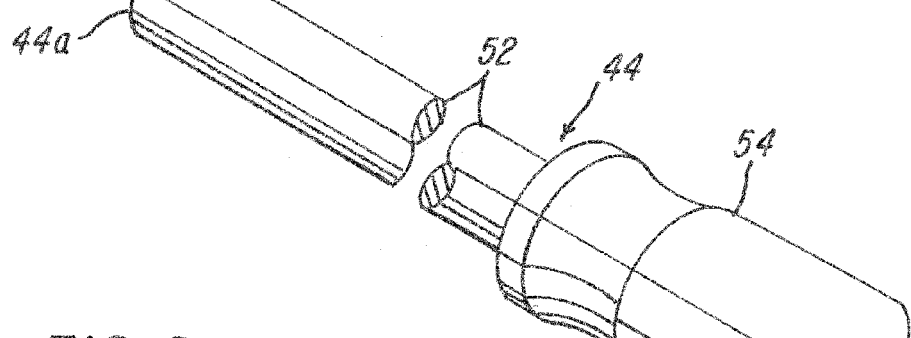
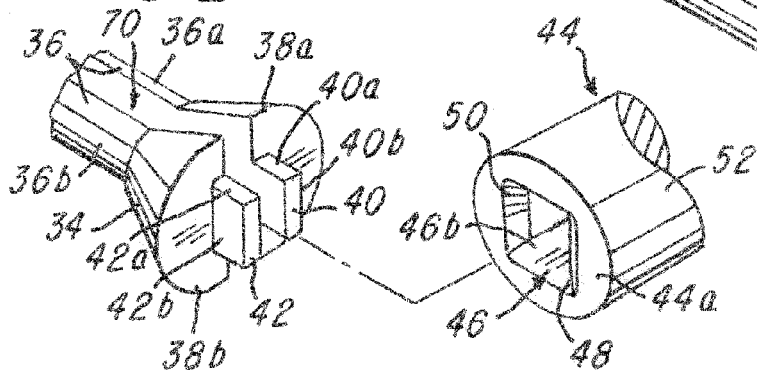

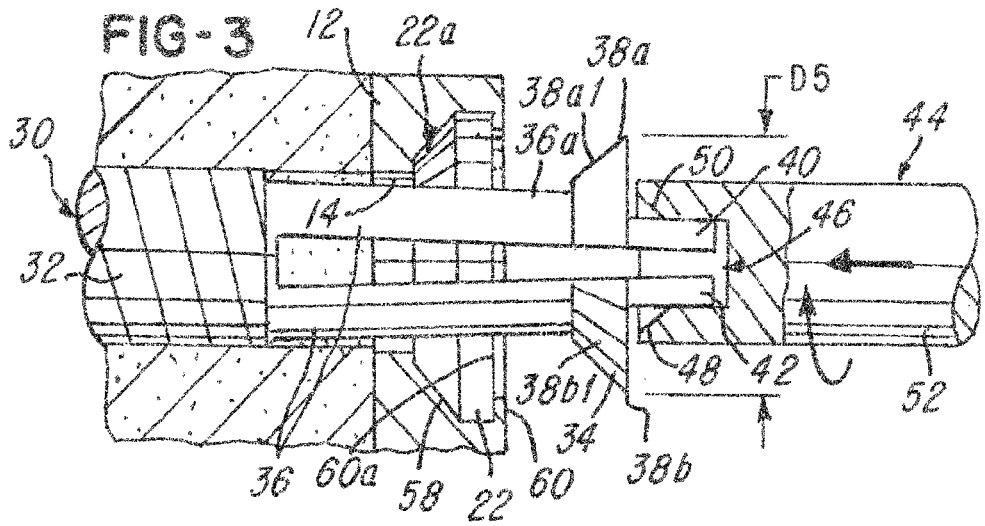
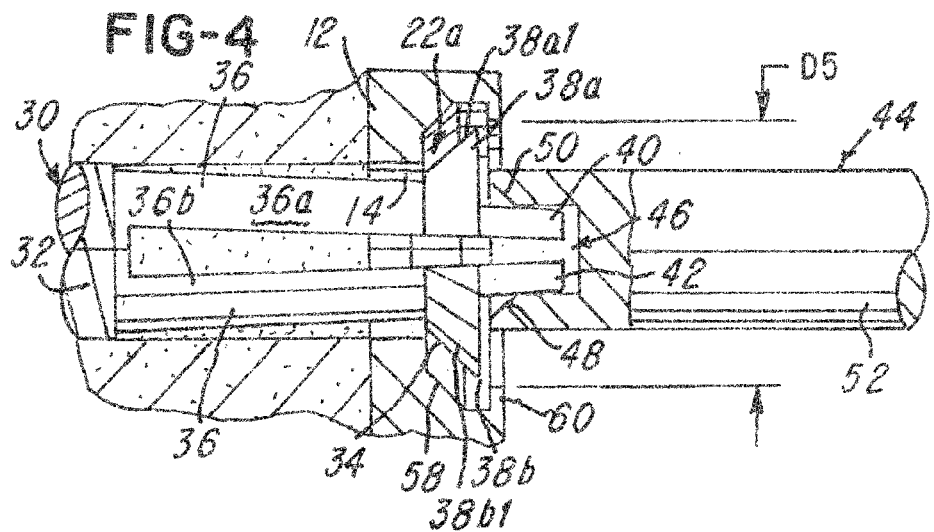
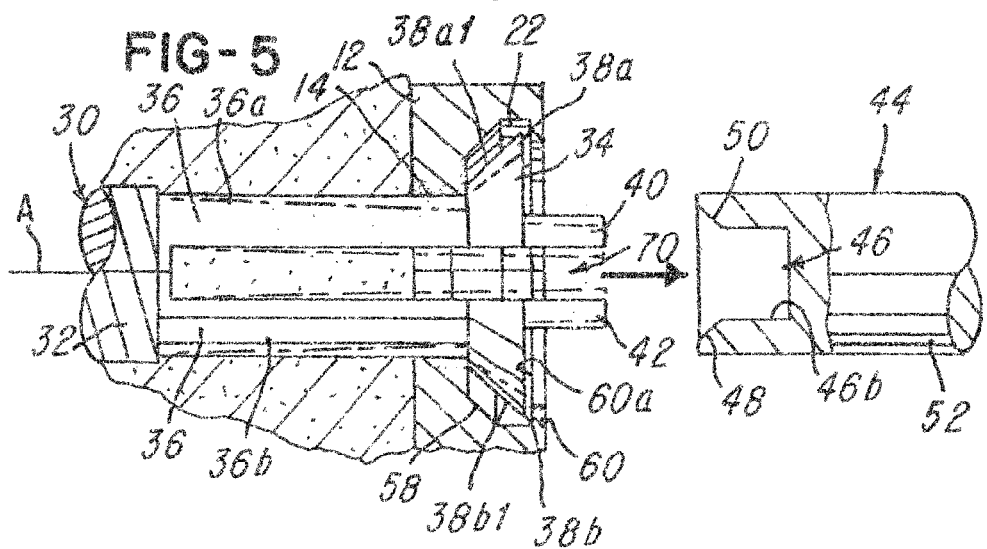

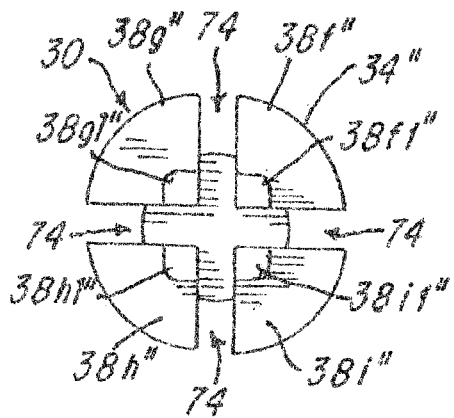
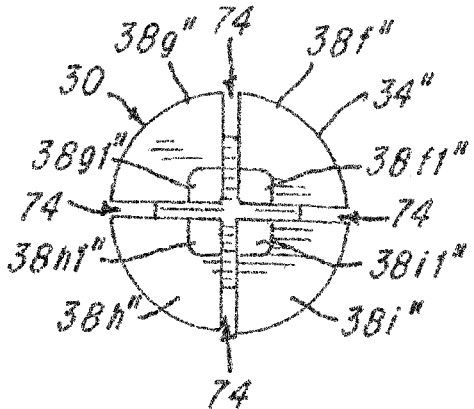
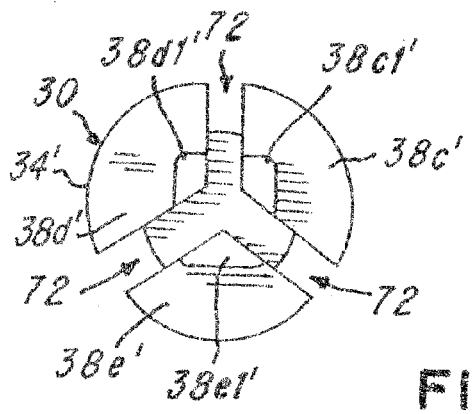
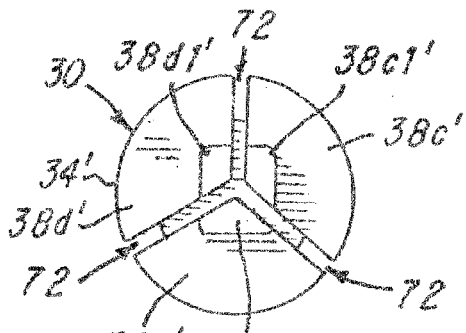
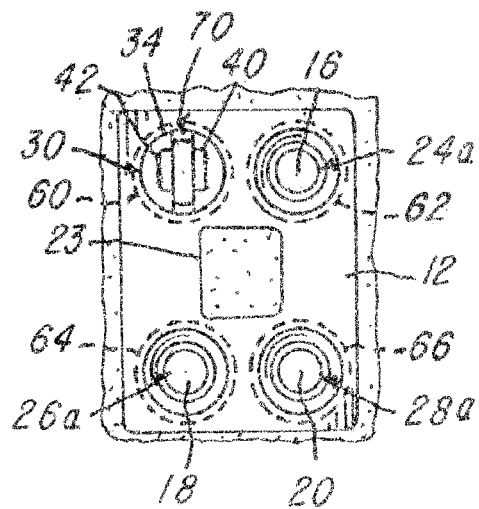

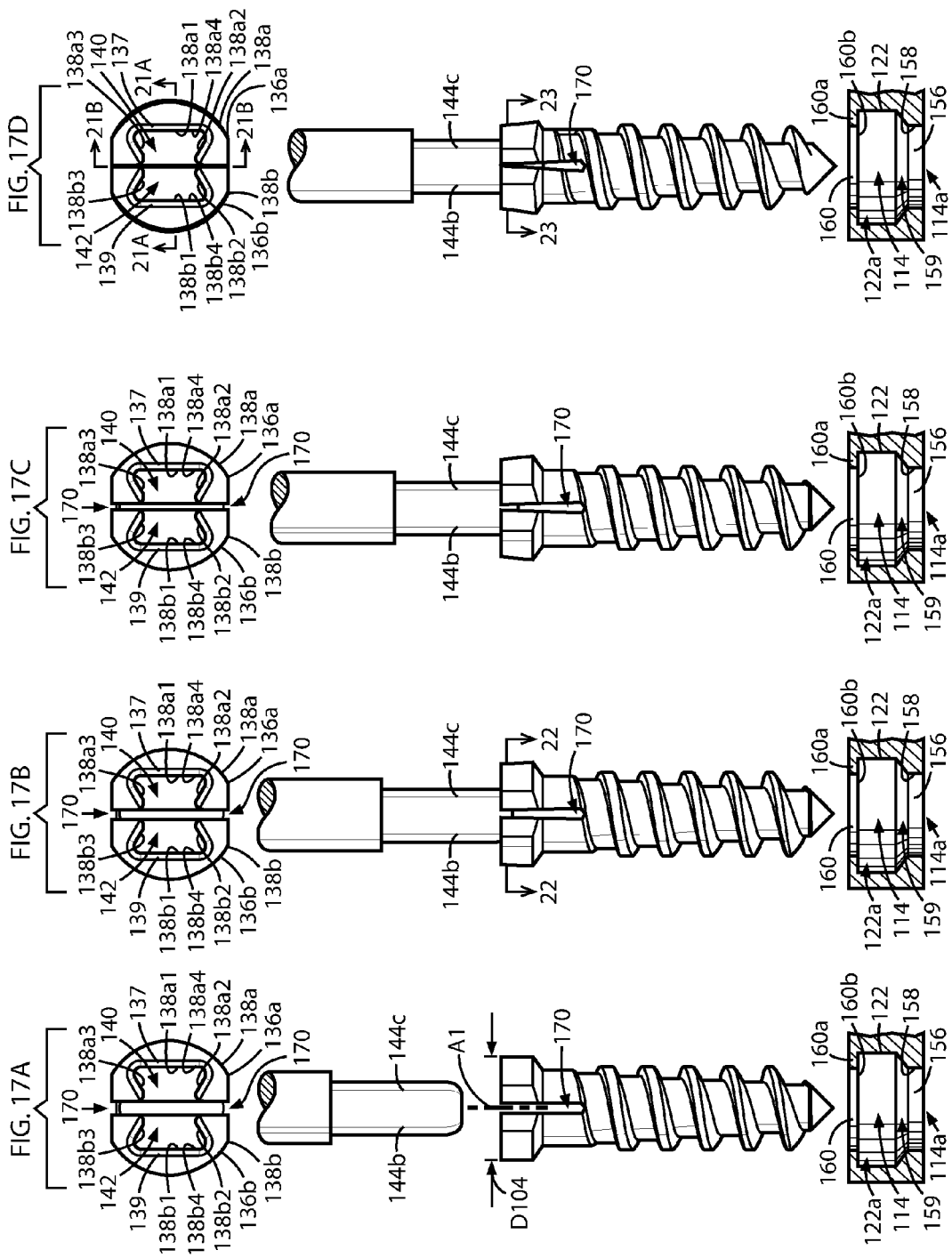

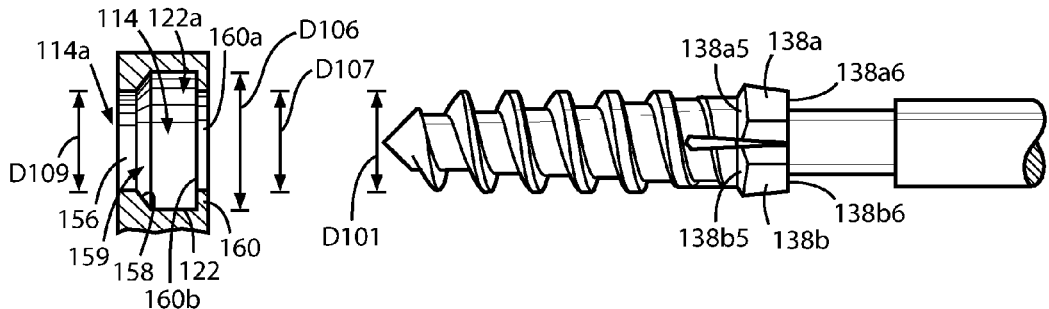
FIG. 18A
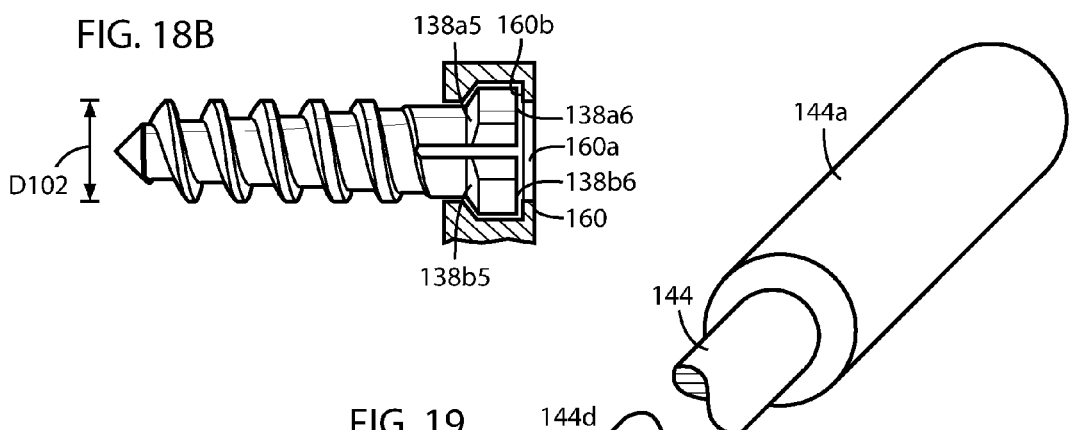
FIG. 18B
FIG. 19
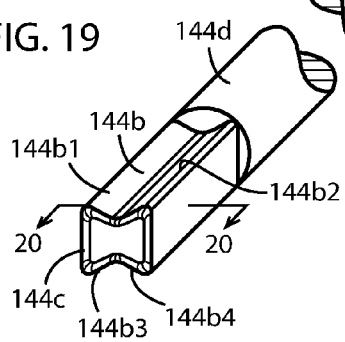
FIG. 20
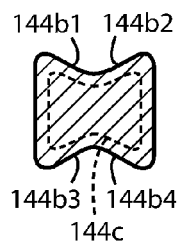

FIG. 21A
FIG. 21B
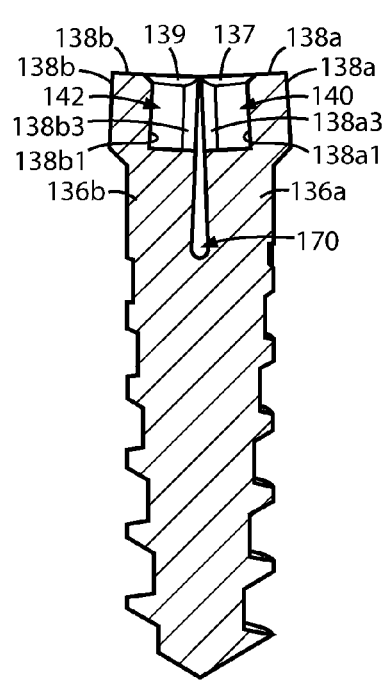
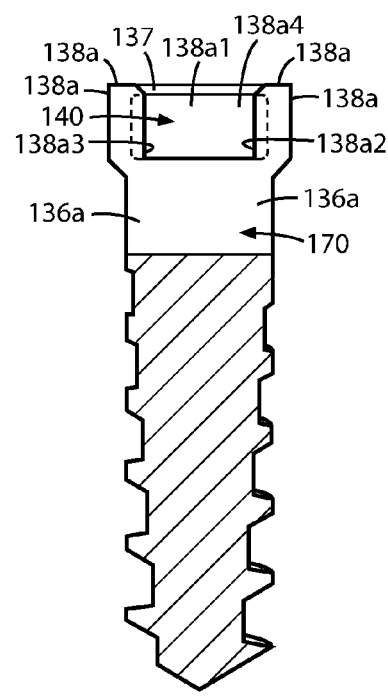
FIG. 22
FIG. 23
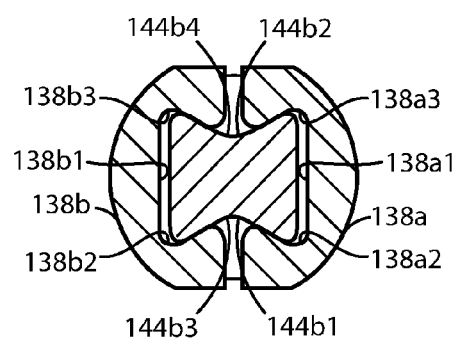
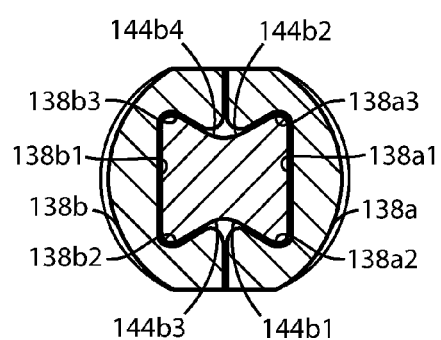

SCREW IMPLANT AND SYSTEM AND METHOD FOR LOCKING A SCREW IN AN IMPLANT PLATE

CROSS-REFERENCE TO RELATED APPLICATION

This application is a continuation-in-part of U.S. patent application Ser. No. 12/612,209, filed Nov. 4, 2009, which issued as U.S. Pat. No. 8,535,356, to which Applicant claims the benefit of the earlier filing date.

BACKGROUND OF THE INVENTION

1. Field of the Invention

This invention relates to surgical implants and, more particularly, it relates to a surgical implant plate and a screw having a screw head having at least a portion that is compressible when a tool, such as a screw driver, engages and compresses the portion of the screw head so that it can be received in the plate. Thereafter, the screw head can expand or decompress in order to lock the screw in the plate upon retraction or dismounting of the tool from the screw head.

2. Description of the Related Art

In the past, various types of implant plates and screw locking mechanisms have been proposed. For example, several surgical implant devices and methods are shown in U.S. Pat. Nos. 4,488,543; 5,192,327; 5,261,911; 5,549,612; 5,713,899; 5,776,196; 6,136,002; 6,159,245; 6,224,602; 6,258,089; 6,261,586; 6,264,655; 6,306,136; 6,328,738; 6,361,537; and 6,592,586. Some or all of these devices have improved the success rate and have simplified the surgical techniques in inter-body vertebral fusion.

U.S. Pat. No. 6,258,089 B1 issued Jul. 10, 2001 to Campbell et al. for an Anterior Cervical Plate and Fixation System discloses an anterior cervical plate, along with threaded fasteners for securing the plate to vertebrae or other osseous material. The cervical plate has several pockets or apertures. The pockets have spherical surfaces, and the fasteners have heads with similarly sized spherical surfaces, which when engaged permit each of the fasteners to be oriented at a variety of projection angles with respect to the plate. In connection with each pocket, the cervical plate incorporates a fastener retaining feature. The feature can take the form of a cantilevered tab or a beam supported at its opposite ends, in each case plastically deformable between an open position for admitting the fastener and a closed position for preventing retraction.

U.S. Pat. No. 5,549,612 issued Aug. 27, 1996 to Yapp et al. for Osteosynthesis Plate System discloses an osteosynthesis plate system that is particularly well adapted to securely fuse adjacent cervical vertebrae. The plates are adapted for mounting upon the anterior or posterior surfaces of the vertebrae. Plates for mounting on the anterior vertebral surfaces have a concave bone contacting surface and a bone screw locking mechanism integral with each screw hole. Moreover, the bone contacting surface of the plate has a plurality of bone penetrating protrusions to more securely affix the plate to bone. Plates for mounting on the posterior vertebral surfaces also have bone penetrating protections on their bone contacting surfaces. Such plates are formed so as to have a curved bone contacting surface that is concave in the transverse axis of the plate and convex in the longitudinal axis of the plate. The screw holes of such plates are constructed so as to guide a bone screw along a desired angle to improve the anchoring of the screws in bone.

One drawback of the plates and screw systems of the past is that they were relatively complicated to machine and manufacture and oftentimes required a large thickness in order to provide enough material that will permit the plate to be machined to provide the integral arms and locks.

What is needed, therefore, is a screw, system and method that reduces the number of steps required to attain a screw-plate locked engagement during a surgical procedure.

SUMMARY OF THE INVENTION

It is, therefore, one object of the invention to provide an integral and compressible screw, system and method having a screw locking mechanism that reduces the number of steps required to attain screw-plate engagement and locking during a surgical procedure.

Another object of the invention is to provide a screw locking system and method that will locate the locking mechanism on the screw, rather than the plate.

Another object of the invention is to provide a screw head having a plurality of screw head portions having internal walls, respectively, that define a plurality of apertures and that cooperate to define a female working opening, the plurality of apertures causing the screw head portions to be urged or compressed together upon the insertion of a tool so that the screw head can be inserted into an aperture in the plate.

Still another object of the invention is to provide a plate system that utilizes a screw having a screw head having a plurality of portions that have camming surfaces that can be used to urge the plurality of portions together upon the insertion of a tool into the female working opening.

Still another object of the invention is to provide a system, method and screw-plate locking mechanism that will permit an improved and simpler plate design and that can, for example, reduce a thickness of the plate or provide other machining and manufacturing advantages.

In one aspect, one embodiment comprises a plate system comprising a plurality of screws, each of the plurality of screws having a shank and the screw head, a plate having a plurality of apertures for receiving the plurality of screws, respectively, the plate further comprising a plurality of the detent portions associated with the plurality of apertures, respectively, the plurality of detent portions defining a plurality of screw head receiving areas associated with the plurality of apertures, respectively, for receiving at least a portion of the screw head after the screw is screwed into bone, the at least a portion of the screw head being adapted to be compressible when the screw is screwed into bone and expandable so that it can be received in at least one of the at least one of the plurality of screw head receiving areas, the at least a portion of the screw head cooperating with at least one of the plurality of detent portions to restrict or prevent the screw from withdrawing from the plate.

In another aspect, another embodiment comprises a method for locking a plurality of screws in a plate and preventing them from withdrawing from the plate, each of the plurality of screws comprising a screw head, the method comprising the steps of providing the plate, the plate having a plurality of apertures and a plurality of receiving areas associated with the plurality of apertures, respectively, providing each screw head with a compressible portion, the compressible portion being resilient and compressible when the screw is screwed into bone and expandable so that the compressible portion can expand and be received in at least one of the plurality of receiving areas, the compressible portion of the screw head of each of the plurality of screws cooperating with at least one of the plurality of receiving areas to which it is associated and preventing the screw from withdrawing from the plate.

In still another aspect, another embodiment comprises a bone screw for use in an implant plate comprising a shank and a bone screw head, the bone screw head comprises a compressible portion, the compressible portion being resilient an compressible when the screw is screwed into bone and expandable so that the compressible portion can expand and be received in at least one of a plurality of receiving areas in the implant plate, the compressible portion of the bone screw head of each of the plurality of screws being compressible when the bone screw is screwed into bone and expandable after it is received in the implant plate in order to prevent the screw from withdrawing from the plate.

In yet another aspect, another embodiment comprises an implant system comprising at least one screw having a screw body having a longitudinal slot or aperture along an axis of the screw body to define a plurality of resilient members, each of the plurality of resilient members comprising an internal wall defining a flexible member aperture, at least a portion of the internal wall defining a camming surface, the flexible member aperture of the plurality of resilient members cooperating to define a tool insertion aperture having a predetermined aperture shape, a tool having a working surface having a predetermined tool shape in cross section that generally complements the predetermined tool aperture shape, the working surface of the tool engaging the camming surface and causing the plurality of resilient members to assume a compressed position.

In another aspect, another embodiment comprises a plate system comprising a plurality of screws, each of the plurality of screws having a shank and a screw head, a plate having a plurality of apertures for receiving the plurality of screws, respectively, the plate further comprising a plurality of detents associated with the plurality of apertures, respectively, at least a portion of the screw head being adapted to be compressible when the at least one of the plurality of screws are screwed into bone and expandable so that it can be received in at least one of a plurality of screw head receiving areas, the at least a portion of the screw head cooperating with at least one of the plurality of detents to restrict or prevent the at least one of the plurality of screws are from withdrawing from the plate.

In still another aspect, another embodiment comprises a method for locking a plurality of screws in a plate and preventing the plurality of screws from withdrawing from the plate, each of the plurality of screws comprising a screw head, the method comprising the steps of providing the plate, the plate having a plurality of apertures and a plurality of receiving areas associated with the plurality of apertures, respectively, providing each screw head with a compressible portion, the compressible portion being resilient and compressible when each of the plurality of screws are screwed into bone and expandable so that the compressible portion can expand and be received in at least one of the plurality of receiving areas, the compressible portion of the screw head of each of the plurality of screws cooperating with the at least one of the plurality of receiving areas to which it is associated and preventing each of the plurality of screws from withdrawing from the plate.

In yet another aspect, another embodiment comprises a bone screw for use in an implant plate comprising a shank and a bone screw head, the bone screw head comprising a compressible portion, the compressible portion being resilient and compressible when the bone screw is screwed into bone and expandable so that the compressible portion can expand and be received in a detent of an implant, the compressible portion of the bone screw head of the bone screw being compressible when the bone screw is screwed into bone and expandable after it is received in the implant plate in order to prevent the bone screw from withdrawing from the implant plate.

In still another aspect, another embodiment comprises an implant system comprising a plate member having a plurality of screw-receiving openings, each of the plurality of screw-receiving openings having at least one plate member detent associated therewith, a plurality of screws each having a screw head having a plurality of integral compressing portions for receipt in the plurality of screw-receiving openings, respectively; and the plurality of integral compressing portions of each screw expanding after the screw is mounted into bone and cooperating with the at least one plate member detent of at least one of the plurality of screw-receiving openings to which it is associated, thereby preventing the screw from withdrawing from the plate member.

These and other objects and advantages of the invention will be apparent from the following description, the accompanying drawings and the appended claims.

BRIEF DESCRIPTION OF THE DRAWINGS

FIG. 1 is a perspective, exploded view of a screw, system and method in accordance with one embodiment of the invention;

FIG. 2 is a fragmentary view illustrating a tool in operative relationship with a compressible head on the screw;

FIG. 3 is a fragmentary view illustrating a screw being received in a plate;

FIG. 4 is a fragmentary view illustrating a portion of the screw being compressed after the screw is received in the tool and as the screw is screwed into the bone;

FIG. 5 is a view of the screw after the tool is removed from the screw head, illustrating the screw head expanding to an expanded and locked position where a surface of at least a portion of the screw head becomes generally opposed to at least one detent, such as a lip, associated with a screw receiving aperture in the plate;

FIG. 8 is a view of the plate illustrating one of the screws locked in the plate after it is driven into bone;

FIG. 11 is a view of another embodiment illustrating the internal concavity in the screw head defining four head portions each having a male projection in a non-compressed state;

FIG. 12 is a view of the alternate embodiment shown in FIG. 11 after the screw head has been compressed, showing the male projections cooperating to define a drivable working surface that can be received in the tool and rotatably driven;

FIG. 13 is a view similar to FIGS. 9 and 11 showing still another embodiment of a screw head in a non-compressed state, with the internal concavity in the screw head defining three screw head portions with each having male projections;

FIG. 14 is another plan view of the screw head shown in FIG. 13 after it has been compressed to a compressed state and showing the male projections cooperating to define a working surface or projection that can be received in and driven by the tool;

FIGS. 17A-17D are fragmentary exploded views illustrating the various positions of the screw head portions and insertion of the tool into the screw head and the closing of the screw head portions in response thereto;

FIGS. 18A and 18B are sectional and fragmentary views illustrating details of one of a plurality of receiving areas in the plate and the insertion and seating of the screw into the plate;

FIG. 19 is a partially broken perspective view illustrating various features of the tool;

FIG. 20 is a sectional view, taken along the line 20-20 in FIG. 19, showing a cross-sectional shape of the tool of FIG. 19;

FIG. 21A is a cross-sectional view, taken along the line 21A-21A in FIG. 17D, illustrating various features of the camming surfaces;

FIG. 21B is a cross-sectional view, taken along the line 21B-21B in FIG. 17D, illustrating features of an internal wall defining an aperture in one of the screw head portions;

FIG. 22 is a cross-sectional view, taken along the line 22-22 in FIG. 17B, illustrating the tool slightly inserted into the screw head portions; and FIG. 23 is a view, taken along the line 23-23 in FIG. 17D, illustrating the screw head portions in a closed position.

DETAILED DESCRIPTION OF THE PREFERRED EMBODIMENTS

Figure 6:
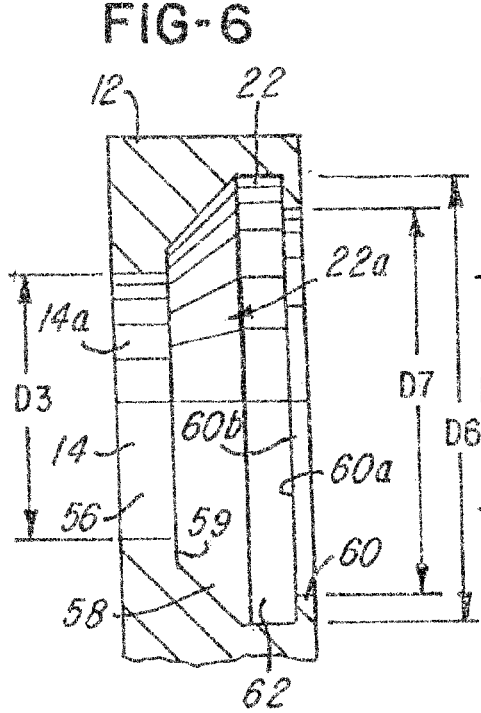
FIG. 6 is a sectional and fragmentary view illustrating details of one of a plurality of receiving areas in the plate.

Referring now to FIGS. 1-14, a system 10 and tool-actuated locking screw mechanism and locking method are shown. The system 10 comprises a plate 12 having a plurality of apertures 14, 16, 18 and 20. The plate 12 may comprise more or fewer apertures if desired and may comprise at least one or a plurality of windows 23 for viewing a graft area (not shown) between two vertebrae to be fused together in a manner conventionally known.

The plurality of apertures 14-20 each comprise an undercut or interior and generally U-shaped wall 22, 24, 26 and 28, respectively, that define a plurality of receiving areas, apertures or undercuts 22a, 24a, 26a and 28a whose purpose and function will be described later herein. For ease of illustration, a sectional fragmentary view of the receiving area 22a is shown and described later herein relative to FIG. 6.

The system 10 comprises at least one or a plurality of screws 30 for securing the plate 12 to at least one or a plurality of vertebrae (not shown). For ease of illustration, a single screw 30 is shown and described, and it should be understood that in the example, a single screw 30 is received in each of the plurality of apertures 14-20. As shown in FIG. 1, each screw 30 comprises a shank or threaded portion 32 and a screw head 34. The screw head 34 comprises at least a portion that is adapted to be elastic, resilient or compressible and define a compressible portion 36. In the embodiment being described, the compressible portion 36 comprises a first elongated portion or resilient portion 36a and a generally opposing second elongated portion or resilient portion 36b as shown. Note that the dimension or diameter D1 (FIG. 7) of the elongated portion 36b is slightly smaller than a diameter D2 (FIG. 1) of the threaded portion 32. The benefit of this design is described later herein.

The screw head 34 further comprises a first head portion 38a that is integrally formed with the first elongated portion 36a as shown and a second head portion 38b that is integrally formed with the second elongated portion 36b as shown. The first and second male projections 40 and 42 are integrally formed with the head portion 38a and 38b, respectively, as shown and extend generally longitudinally in a direction that is generally parallel to an axis of the head.

The system 10 also comprises a tool 44 having a female working opening 46 (FIG. 2) that is adapted to receive and move or compress the first and second male projections 40 and 42 toward each other and toward an axis of the screw 30 when the tool 44 is mounted thereon. The tool 44 comprises an end 44a having an interior recessed area or wall 46b that defines the female aperture or female working opening or area 46. As mentioned, this female working opening 46 is adapted and sized to receive the male projections 40 and 42 and compress them together. Note that the female working opening 46 is adapted, sized and has a shape that generally complements the shape of the male projections 40 and 42 when they are compressed together.

Note that the tool 44 comprises one or more beveled surfaces or chamfers 48 and 50 in communication with the wall 44b that facilitate guiding ends or surfaces 40a and 42a (FIG. 1) into the female working opening 46 and compressing the male projections 40 and 42, respectively, and guiding them toward each other and toward an axis A (FIG. 5) of the screw 30. The tool 44 comprises a shaft 52 which is coupled to or integrally formed with a handle 54 for gripping and rotating the tool 44 and screwing the screw 30 into bone. The tool shaft 52 may be of any desired length, a tool (not shown) with multiple interchangeable shafts (not shown) may be provided, or multiple tools (not shown) having shafts 52 of different lengths.

Returning to the illustration in FIG. 1, it should be understood that the first and second elongated portions 36a and 36b are compressible, resilient and elastic and movable in the direction of double arrow X (FIG. 7) and is adapted to permit compression of at least a portion of the screw head 34 when the tool 44 is engaged with or mounted on the screw head 34. As will be described later herein relative to FIGS. 3-14, removal of the tool 44 from the first and second male projections 40 and 42 results in spontaneous expansion of the at least a portion 36 of the screw head 34, as illustrated in FIGS. 4-5. In the illustration being described, the first and second elongated portions 36a and 36b are elastic and/or resilient and adapted to permit the first and second head portions 38a and 38b, respectively, to move toward each other when the tool 44 is mounted thereon and then permit the first and second male projection portions to decompress, expand or move away from each other when the tool 44 is removed from the screw head 34 in the manner described herein.

As mentioned earlier, the plate 12 comprises the plurality of apertures 14-20 having the associated recessed area or internal concavities 22a-28a, respectively, mentioned earlier. For ease of illustration, the wall 22 and associated receiving area 22a will be shown and described relative to FIG. 6, but it should be understood that each of the other recessed areas or receiving areas 24a-28a are similarly constructed. As illustrated in FIG. 6, the plate 12 has a generally cylindrical wall 56 that defines a generally cylindrical portion or exit area 14a of the aperture 14. Note that the generally cylindrical portion 14a has a diameter D3 (FIG. 6) that is slightly larger than the diameter D2 (FIG. 1) of the threaded portion 32 of screw 30, but smaller than the diameter D4 (FIG. 7) of the screw head portions 38a and 38b when they are in either a compressed or non-compressed state.

The plate 12 further comprises a frusto-conical wall 58 that couples the surface or wall 22 to a radial wall, lip or seat 59 (FIG. 6). The walls 58 and 59 cooperate and are adapted and sized to provide or define a seat for receiving the tapered walls or surfaces 38a1 and 38b1 associated with the screw head portions 38a and 38b, respectively.

The plate 12 comprises a plurality of detents or lips 60, 62, 64 and 66 (FIG. 1) that are integral with the walls 22-28, respectively. The plurality of detents or lips 60, 62, 64 and 66 cooperate with the plurality of walls 22-28, respectively, to define the undercuts or define radial annular part of areas 22a-28a. For ease of illustration, the operation and function of the screw head receiving area 22a and screw 30 will now be described relative to FIGS. 3-7.

In general and as illustrated, the tool 44 (FIGS. 2-4) is mounted on the first and second male projections 40 and 42, which compresses them together as shown in FIGS. 3 and 4. The tool 44 is rotated to screw the screw 30 into bone after the screw 30 is received in the aperture 14 of plate 12. The first and second portions 38a and 38b of screw head 34 comprises surfaces 38a1 and 38b1, respectively. After these surfaces 38a1 and 38b1 move past or clear (FIGS. 4 and 5) the lip or detent 60, the tool 44 may be removed (FIG. 5) from the screw head 34. When the tool 44 is removed from the first and second male projections 40 and 42, the first and second elongated portions 36a and 36b cause the first and second screw head portions 38a and 38b to de-compress or expand into the receiving area, aperture or undercut 22a, as illustrated in FIGS. 4-5.

Figure 7:
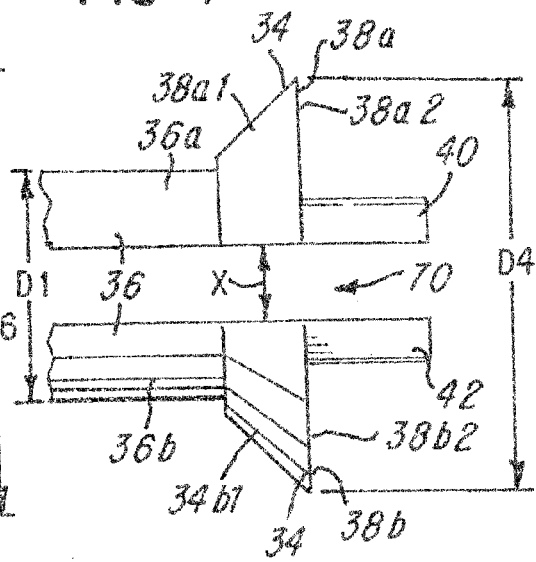
FIG. 7 is a fragmentary view of the screw in a non-compressed state, illustrating various dimensions and configurations of the screw head.

As illustrated in FIGS. 5 and 7, the screw head 34 has an expanded width or screw head diameter dimension D4 (FIG. 7) and a compressed dimension D5 (FIGS. 3 and 4). The wall 22 comprises a wall diameter D6 (FIG. 6) which is larger than the receiving opening dimension or diameter D7 (FIG. 6) defined by an inner surface 60b of the lip or detent 60. In the illustration, dimension D4 (FIG. 7) is larger than dimension D5 (FIG. 4), but smaller than the dimension D6 (FIG. 6), while the compressed dimension D5 is smaller than both the dimension D6 and the dimension D7. This permits the screw head 34 to be received in the aperture 14 and clear the lip 60 when the portions 38a and 38b are compressed, yet be retained by the lip 60 when the portions 38a and 38b are in the non-compressed or expanded state (FIG. 5).

Thus, the tool 44 is mounted on the male projections 40 and 42 of the screw head 34 to compress the screw head 34 by moving the portions 38a and 38b toward each other and toward the axis A (FIG. 5) of the screw 30. The compressed dimension D5, illustrated in FIG. 3, is slightly smaller than the receiving opening dimension D5 so that as the tool 44 is rotated, the screw head 34 clears the lip 60 as the screw 30 becomes screwed into bone. The screw 30 is screwed into bone until the shoulders or surfaces 38a1 and 38b1 clear or move past the surface 60a of the lip 60 as illustrated in FIGS. 3-5. Thereafter, the tool 44 may be removed from the screw head 34 (FIG. 5) which permits the portions 38a and 38b of screw head 34 to resiliently or elastically expand until the surfaces 38a2 and 38b2 (FIG. 7) become generally opposed to the surface 60a of the internal lip or detent 60 as shown in FIG. 5. Notice in FIG. 5 that when this occurs, the surfaces 38a2 and 38b2 cooperate with that surface 60a to retain and lock the screw 30 in the plate 12 and prevent the screw 30 from withdrawing, for example, in an axial direction away from the bone (i.e., to the right as viewed in FIG. 5).

Note in FIG. 5 that the diameter or dimension D1 (FIG. 7) of the screw 30 in the elastic or resilient portions 36a and 36b defines an area or region 37 (FIG. 1) of flexion. This dimension D1 in region 37 is slightly smaller in diameter or cross-section than the diameter or dimension D2 (FIG. 1) of the threaded portion 32. This prevents external bone from engaging and/or compressing the resilient portions 36a and 36b which could interfere with the elastic or resilient re-expansion of the resilient portions 36a and 36b after the tool 44 has been removed from the screw head 34 as illustrated in FIGS. 4 and 5.

At this point, the surfaces 38a2 and 38b2 clear the annular seat or lip 59 before the screw 30 bottoms out. The surgeon then releases the tool 44 and the screw head 34 re-expands. The bottom surface 41 (FIG. 7) of the screw engages the annular seat or lip 59, thereby preventing the screw 30 from travel.

Figure 9:
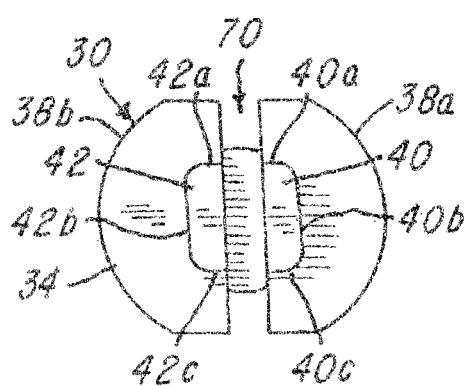
FIG. 9 is a plan view of a screw head in accordance with one embodiment of the invention illustrating an internal concavity or aperture in the screw head which defines a compressible portion on the screw head in the form of a compressible pair of screw head portions each having a male projection.
Figure 10:
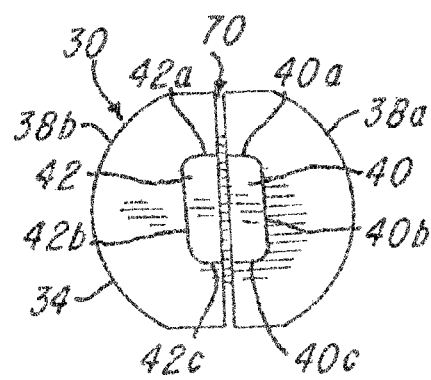
FIG. 10 is a view of the embodiment in FIG. 9 after at least a portion of the screw has been compressed, illustrating the projections cooperating to provide a working surface that can be engaged by a tool and rotatably driven.

In the illustration being described, note that the screw 30 comprises a concavity 70 (FIGS. 1, 2, 9 and 10) that defines the generally opposing first and second elongated portions 36a and 36b and the screw head portions 38a and 38b as shown. As mentioned earlier, the first and second male projection portions 40 and 42 of the screw head 34 are adapted, sized and shaped to provide a rotatably drivable working surface when they are compressed by the working end 44a of the tool 44. In this regard, when the male projections 40 and 42 are compressed toward each other, as illustrated in FIG. 10, they define a generally polygonal shape, such as a rectangular or square shape. The male projections 40 and 42 may also be adapted, sized and shaped to any desired configuration that will enable the at least a portion 36 of the screw head 34, such as the male projections 40 and 42, to be compressed toward the axis of screw 30 or toward each other so that they can be received in the female working opening or area 46 of tool 44 and rotatably driven. Similarly, the interior wall 44b that defines the female aperture or female working opening 46 is adapted, sized and shaped so that it complements the shape of the compressed male projections 40 and 42, so that the male projections 40 and 42 can be rotatably driven by the tool 44 in order to screw the screw 30 into bone, although not shown, The concavity 70 or separating area may comprise one or more separating areas to define the pair of elongated portions 36a and 38a. FIGS. 9 and 10 illustrate the screw 30 having the screw head 34 and concavity 70 that provides or defines the pair of generally opposing male projections 40 and 42 as shown. Again, note that when the screw head portions 38a and 38b are compressed together, the male projections 40 and 42 have surfaces 40a, 40b, 40c and 42a, 42b and 42c (FIGS. 9 and 10) that cooperate to define the generally rectangular (as viewed in FIG. 10) projection that is received in the working end 44a of the tool 44.

FIGS. 13 and 14 illustrate another embodiment showing a screw 30 having a screw head 34' concavity 72 defining three posts, portions or male projections 30c', 30d' and 30e' shown in an expanded state in FIG. 13. Note that when the screw head portions 38c', 38d' and 38e' are compressed toward each other and toward an axis of the screw 30, the associated surfaces of male projections 38c1', 38d1' and 38e1', respectively, and associated surfaces cooperate to define a generally rectangular or polygonal shape. They are adapted to be received by the working end 44a of the tool 44 which has the female aperture or female working opening 46, which is adapted and sized to complement the shape of the male projections when they are compressed so that the tool 44 can rotatably drive and screw the screw 30' into bone.

FIGS. 11 and 12 illustrate yet another illustrative embodiment showing a screw head 34" concavity 74 that defines four generally elongated portions 38f''', 38g''', 38h''' and 38i'''. In this embodiment, each of the four elongated portions 38f'-38i' comprises the male projections portions 38f1'', 38g1'', 38h1'' and 38i1'' as shown in FIG. 11. FIG. 11 illustrates the screw head portions 38f'''-38i''' in their non-compressed or expanded state when they are not engaged by the tool 44. In contrast, FIG. 12 illustrates the compressed state of the screw head portions 38f'''-38i''' after the tool 44 is placed on the male projection portions 38f1''-38i1'' in the manner described earlier herein. Again, it is important to note that the side wall or surfaces of the male projection portions 38f1''-38i1'' cooperate to define a working surface, such as a polygonal, hexagonal, rectangular or square surface that cooperates with and is adapted to be received in the female aperture or female working opening 46 of the tool 44 which has a complementary shape so that the tool 44 can rotatably drive and screw the screw 30 into bone.

While the embodiments shown and described relative to FIGS. 1-14 illustrate two portions 38a and 38b (FIGS. 9 and 10), three portions 30c', 30d' and 30e' (FIGS. 13 and 14) and four portions 38f''', 38g''', 38h''' and 38i''' (FIGS. 11 and 12), it should be understood that the screw head 34 could be provided with a concavity that defines more projection portions if desired.

Returning now to FIG. 6, note that the undercut or receiving area 62 provides a continuous undercut or receiving area 22a about the aperture 14. It should be understood that while the lip 60 in the embodiment being described defines a continuous annular surface 60a surrounding the aperture 14. This lip 60 could also be discontinuous to provide at least one or a plurality of detents that cooperate with one or more of the surfaces 38a2 and 38b2 (FIG. 7) to lock the screw 30 in the plate 12.

Advantageously, a benefit to the embodiments being described herein is a reduction in the number of steps required to remove the screw from the plate screw-plate engagement during a surgical procedure. In this regard, the disengagement of the locking of the screw 30 in the plate 12 occurs when the tool 44 is mounted on the screw head 34. Many prior art systems, for example, require multiple tools, for example, one tool to release the screw lock and another tool to screw the screw.

Moreover, many prior art mechanisms comprised a locking mechanism embodied in the plate or on the plate, whereas the locking mechanism in the illustration being described is embodied and integral with screw 30 rather than the plate. Advantageously, this allows for simpler plate designs. This also permits the plates being made thinner, which is a goal of surgical plate development.

Referring now to FIGS. 15-18B, another embodiment of the invention is shown. In this embodiment a system 100 and tool-actuated locking screw mechanism are shown. In this embodiment, the locking screw mechanism comprises a plate 112 having a plurality of apertures 114, 116, 118 and 120 as shown. The plate 112 may comprise more or fewer apertures if desired and may comprise at least one or a plurality of windows 123 for viewing a graft area (not shown) between two vertebrae to be fused together in a manner conventionally known.

The plurality of apertures 114-120 each comprise an undercut or interior and generally U-shaped wall or channel 122, 124, 126 and 128, respectively, that defines a plurality of apertures, undercuts or receiving areas 122a, 124a, 126a and 128a whose purpose and function will be described later and which function similar to the receiving areas 22a, 24a, 26a and 28a described earlier herein relative to the first embodiment. For ease of illustration, a sectional fragmentary view of wall or channel 122 and receiving area 122a is shown and described later herein relative to FIGS. 18A-18B.

The system 100 comprises at least one or a plurality of screws 130 for securing the plate 112 to at least one or a plurality of vertebrae (not shown). For ease of illustration, a single screw 130 is shown and described and it should be understood that in the example, a single screw 130 is received in each of the plurality of apertures 114-120. As shown in FIGS. 15 and 16A-16C, 17A-17D, 18A-18B and 21A-21B, each screw 130 comprises a threaded portion or shank 132 and a screw head 134. The screw head 134 comprises at least a portion that is adapted to be elastic, resilient or compressible and defines a compressible, elastic or resilient portion 136. In the embodiment being described, the compressible, elastic or resilient portion 136 comprises a resilient portion or elongated portion 136a and a generally opposing second elongated portion or resilient portion 136b as shown. Note that the dimension or diameter of the compressible, elastic or resilient portion 136 may be slightly smaller than a diameter of the threaded portion 132 for the reasons described earlier herein relative to the first embodiment.

The screw head 134 further comprises a first head portion 138a that is integrally formed with the first elongated portion 136a as shown and a second head portion 138b that is integrally formed with the second elongated portion 136b as shown. The first and second head portions 138a and 138b each comprise an interior wall 138a1 and 138b1 that define a female member opening or aperture 140 and a second female member opening or aperture 142 as best illustrated in FIG. 17A. In the embodiment being described, the apertures 140 and 142 defined by the internal walls 138a1 and 138b1 cooperate to define a female opening, slot or female working opening 143 for receiving a tool 144 that will be described later herein. The first and second head portions 138a and 138b are defined by a concavity or separating area 170 that defines and separates the first head portion 138a and the second head portion 138b.

Note that the internal wall 138a1 comprises a first camming surface 138b2 and a second camming surface 138b3 that is joined by a generally flat or planar surface 138b4. Likewise, the interior wall 138b1 of the second head portion 138b comprises or defines a first camming surface 138b2, a second camming surface 138b3 that are joined by a generally planar or flat surface 138b4 as shown.

Note that the interior walls 138a1 and 138b1 comprise a curved, chamfer, beveled or angled surface 137 and 139, respectively, for facilitating insertion of the tool 144 in the manner described later herein. In general, and as illustrated in FIGS. 15 and 16A-16C, note that when the tool 144 is inserted into the female working opening 143, the first and second head portions 138a and 138b are driven or urged together so that the overall dimension of the screw head 134 is reduced so that it can be inserted into the plate 112 in the manner described later herein. Note that the first and second female member openings or apertures 140 and 142 cooperate to define a general bowtie, butterfly or figure-eight shape, especially when the first and second head portions 138a and 138b are in the open or closed position as illustrated in FIG. 17D. Note also the internal walls 138a1 and 138b1 are generally Omega-shaped or U-shaped in cross-section and define an opening such as the curved, chamfer, beveled or angled surface 139 (FIG. 21B) into the female member opening or aperture 140.

Figure 15:
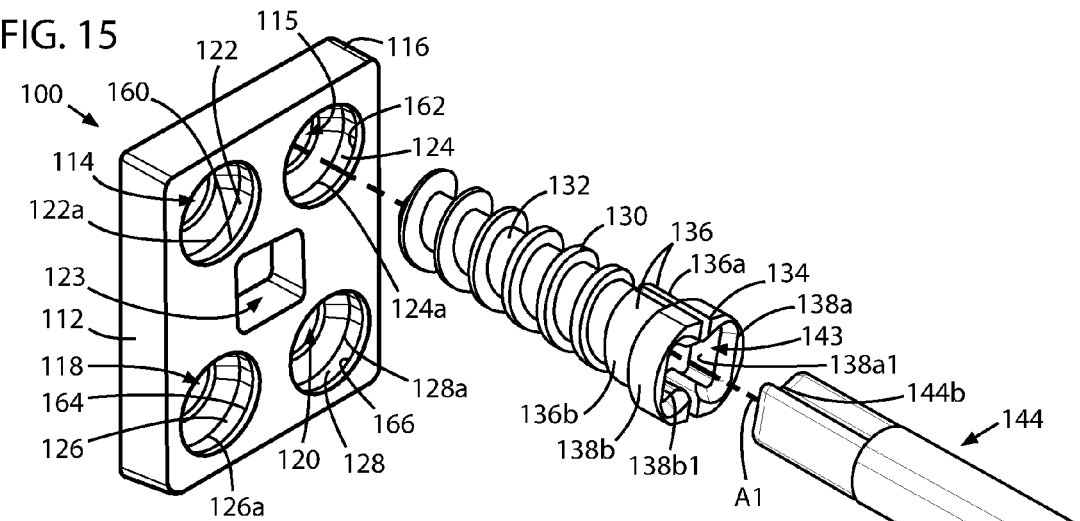
FIG. 15 is a perspective, exploded view of a screw and plate system and method in accordance with another embodiment of the invention.

Referring now to FIGS. 19 and 20, note that the system 100 comprises a tool 144 having a handle 144a and a male working surface 144b. Note that the male working surface 144b also comprises a curved, chamfer, beveled or angled surface 144c (FIG. 19) that cooperates with the curved, chamfer, beveled or angled surfaces 137 and 139 to guide the tool 144 into the female working opening 143 (FIG. 15). It should be understood that when the male working surface 144b is inserted into the female working opening 143, the curved, chamfer, beveled or angled surface 144c engages and cooperates with at least a portion of the curved, chamfer, beveled or angled surfaces 137 and 139 to urge, drive or move the first and second head portions 138a and 138b toward each other as illustrated in FIGS. 16A-16C and 17A-17D and toward an axis A1 (FIG. 17A) of the screw 130.

The tool 144 comprises a tool shaft 144d which is coupled to or integrally formed with the handle 144a for gripping and rotating the tool 144 and screwing the screw 130 into bone. The tool shaft 144d may be of any desired length, a tool (not shown) with multiple interchangeable shafts (not shown) may be provided, or multiple tools (not shown) having shafts 144d of different lengths.

As with the embodiments described earlier herein, it should be understood that the first and second elongated portions 136a and 136b are compressible, resilient and elastic and movable in the direction of double arrow X1 (FIG. 17C) and is adapted to permit compression of at least a portion of the screw head 134 when the tool 144 is received in or mounted in the screw head 134 by inserting the male working surface 144b into the female working opening 143 (FIG. 15).

As with the embodiments described earlier relative to FIGS. 1-14, the first and second elongated portions 136a and 136b are elastic and/or resilient and movable and adapted to permit the first and second head portions 138a and 138b, respectively, to move toward and away from each other when the male working surface 144b of the tool 144 is inserted into the female working opening 143 (FIG. 15), thereby causing the first and second head portions 138a and 138b to move toward each other as illustrated in FIGS. 17A-17D. When the male working surface 144b is removed from the female working opening 143, the first and second elongated portions 136a and 136b and the first and second head portions 13a and 138b decompress, expand or move away from each other and return to their home position, which is illustrated in FIGS. 15 and 17A.

Referring to FIGS. 14 and 18A-18B, the plate 112 comprises the plurality of apertures 114-120 having the associated recessed area or internal concavities 122a-128a, respectively. For ease of illustration, the wall or channel 122 and associated receiving area 122a will be shown and described relative to FIGS. 18A and 18B, but it should be understood that each of the other recessed areas or receiving areas 124a-128a are similarly constructed. As illustrated in FIG. 18A, the plate 112 has a generally cylindrical wall 156 that defines a generally cylindrical portion or exit area 114a of the aperture 114. Note that the generally cylindrical portion 114a has a diameter that is slightly larger than the diameter of the threaded portion 132 of the screw 130, but smaller than the diameter of the screw head portions 138a and 138b when they are in either a compressed or decompressed state.

The plate 112 further comprises a frusto-conical wall 158 that couples the surface or wall 122 to the generally cylindrical wall 156 to define a seat or area 159. The walls 158 and 122 cooperate and are adapted in size to provide or define a seat for receiving tapered walls or surfaces 138a5 and 138b5 associated with the screw head portions 138a and 138b, respectively.

The plate 112 comprises a plurality of detents or lips 160, 162, 164 and 166 (FIG. 15) that are integral with the walls 122-128, respectively. The plurality of detents or lips 160, 162, 164 and 166 cooperate with the plurality of walls 122-128, respectively, to define the undercuts, channels or receiving areas 122a-128a. For ease of illustration, the operation and function of one of the undercuts, channels or receiving areas 122a-128a, namely, the screw head undercut, channel or receiving area 122a and associated detent or lip 160 and screw 130, will now be described.

In general and as illustrated in FIGS. 16A-16C and 17A-17D, the tool 144 is mounted in or received in the screw head 134 by inserting the male working surface 144b of the tool 144 into the female working opening 143. As the male working surface 144b is aligned with the female working opening 143, as illustrated in FIG. 17A, the tool 144 is guided or driven axially into the screw head 134 until the curved, chamfer, beveled or angled surface 144c of the male working surface 144b engages at least a portion of the curved, chamfer, beveled or angled surfaces 137 and 139 of the first and second head portions 138a, 138b as illustrated in FIGS. 17B and 22. As the male working surface 144b is driven further into the female working opening 143, the male working surface 144b and the curved, chamfer, beveled or angled surfaces 137 and 139 cooperate to urge the screw head portions 138a and 138b closer together as shown in FIGS. 16A-16C, 17B-17D and 22-23. Note in FIGS. 17D and 23, when the male working surface 144b is at least partially in the female member openings or apertures 140 and 142, and generally after the curved, chamfer, beveled or angled surfaces 144c of has cleared the curved, chamfer, beveled or angled surfaces 137 and 139, the screw head portions 138a and 138b are fully compressed or urged together and may engage as shown in FIGS. 17D and 23, which reduces an overall dimension or diameter of the screw head 134 so that it can be inserted into the aperture 114 (FIG. 18A), for example, and past the detent or lip 160. Once the screw 130 is mounted onto the tool 144, the screw 130 and tool 144 can be driven axially or moved into the aperture 114 as illustrated in FIG. 18A. Note that the screw head 134 has an expanded or uncompressed width or screw head diameter dimension D104 (FIG. 17A) when in the home position and a compressed or reduced dimension D105 (FIG. 17D) when in the compressed position. The wall or channel 122 comprises a diameter which is larger than the receiving aperture 114 dimension or diameter D107 defined by the inner surface 160a of the detent or lip 160. Note, however, that the dimension D104 (FIG. 17A), which is the dimension of the first and second head portions 138a and 138b in an uncompressed state, is larger than the dimension D109 (FIG. 18A) of the exit area 114a defined by wall 156, but is slightly smaller than the dimension D106, associated with the diameter of the wall 122. In contrast, the compressed dimension D105 (FIG. 17D) is smaller than both the dimensions D106 and D107. This permits the screw head 134 to be received in the aperture 114 and clear the detent or lip 160 when the screw head portions 138a and 138b are compressed together as illustrated in FIGS. 17D and 18A, yet be retained by the detent or lip 160 when the tool 144 is removed from the screw head 134 and the screw head portions 138a and 138b are in the non-compressed or expanded state illustrated in FIGS. 17A and 18B.

Thus, the male working surface 144b of the tool 144 is mounted in the female working opening 143 defined by the female member openings or apertures 140 and 142 to compress the screw head 134 by moving or urging the screw head portions 138a and 138b toward each other and toward the axis A1 (FIG. 17A) of the screw 130. The compressed dimension D105, illustrated in FIGS. 17D and 18A, is slightly smaller than the receiving opening dimension D107 (FIG. 18A) so that as the tool 144 is rotated, the screw head 134 clears the detent or lip 160 as the screw 130 becomes screwed into bone. The screw 130 is screwed into bone until the shoulders or surfaces 138a6 and 138b6 clear or move past a surface 160a of the internal detent or lip 160 in a manner similar to the embodiment described earlier herein relative to FIGS. 1-14. When the tool 144 is removed from the screw head 134, the first and second elongated portions 136a and 136b and the screw head portions 138a and 138b of the screw head 134 resiliently or elastically expand to the decompressed home position illustrated in FIG. 18B, whereupon the surfaces 138a6 and 138b6 become generally opposed to the surface 160b of the internal detent or lip 160 as illustrated in FIG. 18B. Note that when this occurs, the surfaces 138a6 and 138b6 cooperate with that surface 160b and lip 160 to retain and lock the screw 130 in the plate 112 and prevent the screw 130 from withdrawing, for example, in an axial direction away from bone (i.e., to the right as viewed in FIG. 18B).

Note in FIG. 18B that the diameter or dimension of the screw 130 in the elastic or resilient elongated portions 136a and 136b define an area of flexion. As with the first embodiment, the dimension of this area of flexion may be slightly smaller in diameter or cross-section than the diameter or dimension of the threaded portion or shank 132. This facilitates preventing external bone from engaging and/or compressing the resilient elongated portions 136a and 136b which could interfere with the elastic or resilient expansion of the resilient elongated portions 136a and 136b after the tool 144 has been removed from the screw head 134 as illustrated in FIG. 18B.

Again, the surfaces 138a6 and 138b6 clear the detent or lip 160 before the screw 130 bottoms out in the seat or area 159. The bottom surfaces 138a5 and 138b5 engage the seat or wall 159, thereby preventing the screw 130 from further travel. The surgeon then releases the tool 144 and the screw 130 re-expands or decompresses as described.

Note that in this embodiment, the screw 130 comprises the concavity area 170 (FIGS. 17A-17D) that defines the generally opposing first and second elongated portions 136a and 136b and the screw head portions 138a and 138b as shown. As mentioned earlier, the inner walls 138a1 and 138b1 that define the female member openings or apertures 140 and 142 are adapted, sized and shaped and cooperate to provide the female working opening 143 for receiving the male working surface 144b of the tool 144 so that as the tool 144 is inserted in the female working opening 143, the screw head portions 138a and 138b become compressed together as illustrated in FIGS. 16A-16C and 17B-17D. The inner walls 138a1 and 138b1 define the generally opposing female member openings or apertures 140 and 142 that are in fluid communication and open toward each other as illustrated in FIGS. 17A-17D. In the illustration being described, the apertures have the same shape, but it should be understood that they could comprise different shapes if desired. An important feature of the inner walls 138a1 and 138b1 is that they define the camming surfaces 138a2, 138a3 and 138b2, 138b3 (FIGS. 17A-17D), respectively. Note that as illustrated in FIG. 20, that the male working surface 144b of the tool 144 has a common or similar shape in cross-section and is roughly the same size as the female working opening 143 when the first and second head portions 138a and 138b are in the closed or compressed position illustrated in FIG. 17D. Note that as the male working surface 144b is inserted progressively axially into the female working opening 143, the first and second screw head portions 138a and 138b are driven toward each other. To perform this compression or driving movement, note that the male working surface 144b comprises a plurality of camming surfaces 144b1, 144b2, 144b3 and 144b4 that engage the camming surfaces 138b2, 138b3, 138a2 and 138a3, respectively, as illustrated in FIGS. 22-23. As the male working surface 144b is driven into the female working opening 143, the camming surfaces 144b1 and 144b2 cam and engage the camming surfaces 138a2 and 138a3, respectively, while the camming surfaces 144b3 and 144b4 cam and engage the camming surfaces 138b2 and 138b3, respectively, along with the angled, beveled or chamfer surface 144c and curved, chamfer, beveled or angled surfaces 137 and 139 and urge the screw head portions 138a and 138b together until they reach a fully compressed position illustrated in FIGS. 16C, 17D and 18A.

Figure 16A:
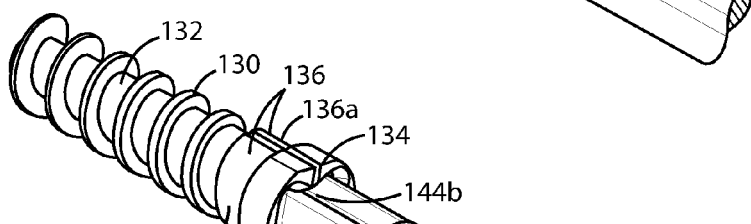
FIGS. 16A-16C are perspective views illustrating the insertion of a working surface of a tool into a female working opening of various portions of a screw head of the screw.
Figure 16B:
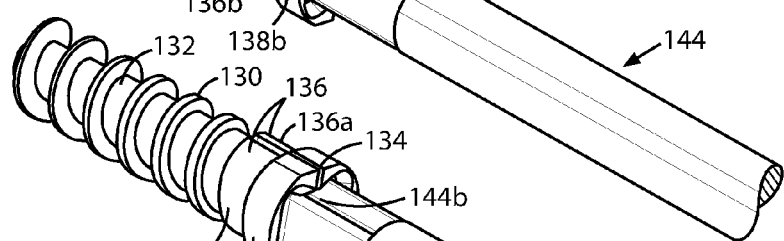
Figure 16C:
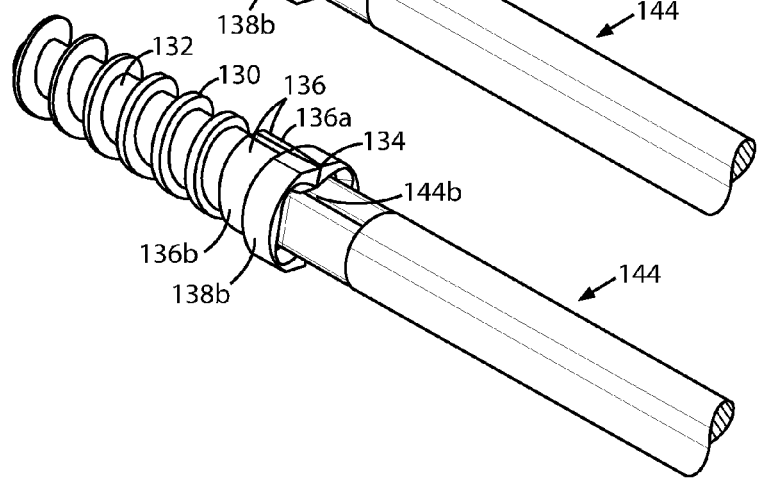

As mentioned earlier, to facilitate insertion of the male working surface 144b into the female working opening 143, the tool 144 has the angled, beveled or chamfer surface 144c (FIG. 19) that engages the similarly shaped curved, chamfer, beveled or angled surfaces 137 and 139 (FIG. 17A), which facilitates guiding the male working surface 144b into the female working opening 143. The curved, chamfer, beveled or angled surfaces 137, 139 and 144c, also cooperate to guide the various camming surfaces with the surfaces 144b1, 144b2, 144b3 and 144b4, respectively, into engagement with the camming surfaces 138a2, 138a3, 138b2 and 138b3, respectively. In one embodiment, by the time the angled, beveled or chamfer surface 144c has passed the curved, chamfer, beveled or angled surfaces 137 and 139, the first and second head portions 138a and 138b are in the compressed state, as illustrated in FIGS. 16C and 17D. Thus, it should be appreciated that the female working opening 143 is adapted and shaped by the inner walls 138a1 and 138b1 which are generally mirror images of each other in the illustration being described and which cooperate to provide the means and camming surfaces that are adapted to cooperate with the camming surfaces 144b1-144b4 to cause the first and second head portions 138a and 138b to be driven or urged together when the male working surface 144b of the tool 144 is inserted into the female working opening 143.

It should be appreciated that the female member openings or apertures 140 and 142, which are defined by the inner walls 138a1 and 138b1 are shown as being substantially the same shape and size, but it should be appreciated that they could comprise other shapes and configurations and that they do not have to be generally the same so long as they provide means and apparatus, such as the camming surfaces 138a2, 138a3, 138b2 and 138b3 for driving the first and second head portions 138a and 138b together upon insertion of the male working surface 144b of the tool 144. Of course, if the female working opening 143 changes in size, shape or configuration, the generally complementary-shaped male working surface 144b would also be adapted, sized and shaped to complement the shape of the female working opening 143.

The concavity or separating area 170 illustrated in FIG. 17A, for example, comprises one separating area that defines the first and second pair of elongated portions 136a and 136b, but it should be appreciated that more separating areas could be provided so that additional elongated members (not shown) are provided. For example, the configuration of the elongated members could be similar to that shown in the embodiments of FIGS. 11-14 which define more than two elongated members. Of course, each of the head portions (not shown) of those elongated members would have an internal or inner wall (not shown) that defines an aperture and camming surfaces that would be used with a complementary shaped tool such that when the working surface of the tool is inserted into the apertures, it urges the screw head portions together in the manner described herein.

As mentioned earlier herein relative to FIG. 6, the embodiment shown in FIG. 18A provides the detent or lip 160 that provides a continuous undercut or receiving area 122a about the aperture 114. It should be understood that while the detent or lip 160 in the embodiment described relative to FIG. 18A defines a continuous annular or radial surface 160b surrounding the aperture 114, this detent or lip 160 could also be discontinuous to provide at least one or a plurality of detents that cooperate with one or more of the surfaces 138a6 and 138b6 to further lock the screw 130 in the plate 112.

Advantageously, one additional benefit to the embodiments being described herein is a reduction in the number of steps required to remove the screw 130 from the plate 112. In this regard, the disengagement of the locking of the screw 130 in the plate 112 occurs when the tool 144 is inserted into the screw head 134 as described herein and the bone screw 130 is unscrewed from the bone. As mentioned earlier, many prior art systems require multiple tools, for example, one tool to release the screw lock and another tool to screw or unscrew the screw.

Another advantageous feature of the embodiment described herein is that the male projection, such as the male projections 40 and 42 in the embodiment described relative to FIGS. 1-14, are eliminated and a female aperture or female working opening 143 is provided. Also, the female working opening 46 of the first embodiment is also eliminated. Replacing the male projections 40 and 42 with the female working opening 143 of the first embodiment facilitates providing a more compact design with less protrusions from the screw head 134 or extending from the plate 112.

While the system, apparatus and method herein described, and the form of apparatus for carrying this method into effect, constitute preferred embodiments of this invention, it is to be understood that the invention is not limited to this precise method and form of apparatus, and that changes may be made in either without departing from the scope of the invention, which is defined in the appended claims.

What is claimed is:

1. A bone screw for use in an implant plate comprising:
a shank and a bone screw head;
said bone screw head comprising a compressible portion, said compressible portion being resilient and compressible when said bone screw is screwed into bone and expandable so that said compressible portion can expand after it is received in a detent of said implant plate in order to prevent said bone screw from withdrawing from said implant plate;
wherein said compressible portion comprises a plurality of screw head portions that are compressible or movable toward a central longitudinal axis of said bone screw and to a compressed position in response to a tool being inserted into said screw head;
wherein each of said plurality of screw head portions are elastic or resilient and have an inner wall that defines an opening, said opening of said plurality of screw head portions cooperate to define a female tool-receiving opening for receiving a working surface of said tool, at least a portion of said inner wall defining a camming surface that is adapted to be engaged by said working surface of said tool when said tool is inserted axially into said female tool-receiving opening, thereby driving said plurality of screw head portions into a compressed position when said bone screw is inserted into said implant plate;
wherein said plurality of screw head portions are normally in an unbiased or undeflected home position when said tool is not inserted into said bone screw head so that after said bone screw head is inserted into said implant plate and said tool is removed from said female tool-receiving opening, said plurality of screw head portions return to said unbiased or undeflected home position and becomes operatively associated with said detent;
wherein each of said inner walls cooperate to define a female opening having a predetermined configuration when said plurality of resilient portions are moved or urged together;
said working surface of said tool having a cross-sectional shape that generally complements said predetermined configuration of said female opening so that when said working surface is inserted into said female opening, it compresses or urges said plurality of resilient portions together so that the overall dimension of the screw head is reduced, and said tool can substantially simultaneously be used to rotatably drive said screw.

2. The bone screw as recited in claim 1 wherein said inner wall or surface is generally U-shaped or Omega-shaped in cross-section that is generally radial with respect to said central longitudinal axis of said bone screw.

3. The bone screw as recited in claim 1 wherein said predetermined configuration is generally bowtie, butterfly or figure eight shaped or generally Omega shaped.

4. The bone screw as recited in claim 1 wherein each of said inner walls comprises a curved or beveled surface adapted to facilitate introducing said working surface of said tool into said female tool-receiving opening and into engagement with said camming surface.

5. The bone screw as recited in claim 1 wherein said working surface of said tool comprises a beveled or curved surface for engaging said camming surface.

6. The bone screw as recited in claim 1 wherein said camming surface extends generally radially inwardly toward said central longitudinal axis of said bone screw.

7. The bone screw as recited in claim 1 wherein said inner wall is non-circular and comprises at least one raised or inwardly-sloped projection surface that defines said camming surface.

8. The bone screw as recited in claim 1 wherein said plurality of screw head portions are dimensioned such that when they are in said compressed position said bone screw head clears at least one detent in a plate in which said bone screw is inserted.

9. The bone screw as recited in claim 1 wherein each of said plurality of screw head portions is generally elongated and has a central longitudinal axis that is generally parallel to said central longitudinal axis of said shank.

10. The bone screw as recited in claim 1 wherein said bone screw head has an interrupted or discontinuous inner wall that defines a plurality of female openings in said plurality of screw head portions, respectively, said plurality of female openings cooperating to define a female working opening for receiving said tool such that when said tool is inserted into said female working opening said plurality of screw head portions are driven together to reduce a dimension of said bone screw head.

11. The bone screw as recited in claim 10 wherein said interrupted or discontinuous inner wall has a camming surface that may be engaged by a working surface of said tool when said tool is inserted into said female working opening thereby driving said plurality of screw head portions together to a compressed position.

12. The bone screw as recited in claim 11 wherein said interrupted or discontinuous inner wall is generally U-shaped or Omega-shaped in cross section.

13. The bone screw as recited in claim 11 wherein said interrupted or discontinuous inner wall cooperates to define said female working opening having a predetermined shape that is adapted to receive a working end of said tool which has a generally complementary shape so that when said tool is inserted into said female working opening, said plurality of screw head portions are driven to said compressed position and said tool can simultaneously be used to screw said bone screw into bone.

14. The bone screw as recited in claim 13 wherein said predetermined shape is generally figure eight or bowtie shaped.

15. The bone screw as recited in claim 1 wherein said plurality of screw head portions are elongated and comprise a central longitudinal axis that is generally parallel to said central longitudinal axis of said bone screw.

16. The bone screw as recited in claim 1 wherein said plurality of screw head portions comprises a first portion that generally opposes a second portion.

17. The bone screw as recited in claim 1 wherein each of said plurality of screw head portions comprise a first end integrally formed in said shank of said bone screw and a free end that is adapted to be moved toward and away from said central longitudinal axis of said bone screw.

18. The bone screw as recited in claim 1 wherein said working surface substantially simultaneously engages said plurality of camming surfaces of said inner wall surface of each of a plurality of screw head portions on said compressible portion.

19. A plate system comprising:
a plurality of screws, each of said plurality of screws having a shank and a screw head;
a plate having a plurality of apertures for receiving said plurality of screws, respectively, said plate further comprising a plurality of detents associated with said plurality of apertures, respectively;
a tool having a working surface for compressing at least a portion of said screw head after said at least a portion of said screw head receives said working surface;
said at least a portion of said screw head being adapted to be compressible so that it can be received in at least one of a plurality of screw head receiving areas in said plurality of apertures, respectively, said at least a portion of said screw head comprising a plurality of resilient portions each comprising an inner wall, at least a portion of said inner wall defines a camming surface that is adapted to be engaged by said working surface of said tool to drive said plurality of resilient portions together to a compressed position when said tool is inserted into said screw head, said compressed position enabling said screw head to clear said at least one of said plurality of detents when said screw is inserted into said plate, said working surface of said tool also driving said screw head in response to a rotation of said tool;
wherein said plate comprises at least one detent associated with each of said plurality of apertures so that each aperture has at least one detent associated therewith;
said at least a portion of said screw head cooperating with at least one of said plurality of detents to restrict or prevent said at least one of said plurality of screws are from withdrawing from said plate after said at least a portion of said screw head is received in said at least one of said plurality of screw head receiving areas;
wherein when said working surface is removed from said screw head, said plurality of resilient portions become decompressed or expanded so that at least one of said plurality of resilient portions becomes generally opposed to said plurality of detents;
wherein each of said inner walls cooperate to define a female opening having a predetermined configuration when said plurality of resilient portions are moved or urged together;
said working surface of said tool having a cross-sectional shape that generally complements said predetermined configuration of said female opening so that when said working surface is inserted into said female opening, it compresses or urges said plurality of resilient portions together so that the overall dimension of the screw head is reduced, and said tool can substantially simultaneously be used to rotatably drive said screw.

20. The plate system as recited in claim 19 wherein each of said inner walls are generally U-shaped in cross-section.

21. The plate system as recited in claim 19 wherein said working surface of said tool comprises a beveled or curved surface for engaging said camming surface and for causing said plurality of resilient portions to assume said compressed position.

22. The plate system as recited in claim 21 wherein each of said inner walls comprises a curved or beveled surface adapted to facilitate introducing said working surface of said tool into said female opening and for engaging said camming surface.

23. The plate system as recited in claim 19 wherein said working surface of said tool comprises a beveled or curved surface for engaging said camming surface and each of said inner walls comprises a curved or beveled surface adapted to facilitate introducing and guiding said working surface of said tool into engagement with said camming surface.

24. The plate system as recited in claim 19 wherein said plurality of resilient portions are normally in an unbiased or undeflected home position when said tool is not inserted into said screw head so that after said screw head clears said at least one of said plurality of detents and said tool is removed from said female opening, said plurality of resilient portions return to said unbiased or undeflected home position, whereupon at least a portion of at least one of said plurality of resilient portions becomes operatively associated with at least one of said plurality of detents, thereby locking said screw in said plate.

25. The plate system as recited in claim 19 wherein each of said camming surfaces extends generally radially inwardly toward a central longitudinal axis of said screw.

26. The plate system as recited in claim 19 wherein said inner wall is non-circular and comprises at least one raised or inwardly-projecting projection surface that defines said camming surface.

27. The plate system as recited in claim 19 wherein said inner wall is not circular and defines or provides a plurality of inner walls in said plurality of resilient portions, respectively, said plurality of inner walls having a plurality of camming surfaces, respectively, that may be engaged by a plurality of working portions of said working surface of said tool when said tool is inserted into a female working opening, thereby driving said plurality of screw head portions together.

28. The plate system as recited in claim 27 wherein each of said plurality of inner walls is generally U-shaped or Omega-shaped in cross section.

29. The plate system as recited in claim 19 wherein said predetermined configuration is a figure eight or bowtie shape.

30. The plate system as recited in claim 27 wherein said tool cross-sectional shape is adapted to have engaging surfaces for engaging said camming surfaces in order to drive said plurality of screw head portions to said compressed position.

31. The plate system as recited in claim 30 wherein said predetermined shape is a figure eight or bowtie shape in cross section.

32. The plate system as recited in claim 19 wherein said plurality of detents comprise a plurality of undercut walls, respectively, that define a plurality of undercuts associated with said plurality of apertures, respectively, each of said plurality of undercut walls defining a receiving area for receiving at least a portion of said plurality of resilient portions.

33. The plate system as recited in claim 19 wherein each of said plurality of detents defines a generally U-shaped wall that defines an undercut associated with each of said plurality of apertures, said generally U-shaped wall defining a generally U-shaped receiving area for receiving at least a portion of said plurality of resilient portions.

34. The plate system as recited in claim 19 wherein said plurality of resilient portions extend generally longitudinally and parallel to a central longitudinal axis of said shank.

35. The plate system as recited in claim 34 wherein said plurality of resilient portions comprises a first portion that generally opposes a second portion.

\* \* \* \* \*